(12) United States Patent
Blais et al.

(10) Patent No.: US 11,169,129 B2
(45) Date of Patent: Nov. 9, 2021

(54) SYSTEM AND METHOD FOR CALIBRATING INSPECTION OF A FEATURE ON A PART

(71) Applicant: PRATT & WHITNEY CANADA CORP., Longueuil (CA)

(72) Inventors: Mario Blais, Varennes (CA); Clement Drouin Laberge, Terrebonne (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 0 days.

(21) Appl. No.: 16/793,633

(22) Filed: Feb. 18, 2020

(65) Prior Publication Data
US 2021/0255155 A1    Aug. 19, 2021

(51) Int. Cl.
*G01N 33/00*     (2006.01)
(52) U.S. Cl.
CPC ..... *G01N 33/00* (2013.01); *G01N 2033/0078* (2013.01)
(58) Field of Classification Search
CPC ..................... G01N 33/00; G01N 2033/0078
See application file for complete search history.

(56) References Cited

U.S. PATENT DOCUMENTS

| 7,448,271 B2 | 11/2008 | Duncan et al. | |
| 2016/0161250 A1* | 6/2016 | Nakamura | G01B 11/2416 356/610 |
| 2017/0129039 A1* | 5/2017 | Williams | B23K 10/006 |
| 2018/0211373 A1* | 7/2018 | Stoppa | G06K 9/4628 |
| 2019/0258225 A1* | 8/2019 | Link | G06T 19/20 |
| 2019/0338666 A1 | 11/2019 | Finn et al. | |
| 2019/0339165 A1* | 11/2019 | Finn | F01D 21/003 |

FOREIGN PATENT DOCUMENTS

KR     20150128300 A     11/2015

* cited by examiner

*Primary Examiner* — Paul M. West
*Assistant Examiner* — Mark Ashabman
(74) *Attorney, Agent, or Firm* — Norton Rose Fulbright Canada LLP

(57) ABSTRACT

Methods and systems for calibrating inspection of a feature on a part are described. The method comprises acquiring, at a plurality of point cloud densities, measurement data from a reference part having a known defect associated with the feature; assessing the measurement data at the plurality of point cloud densities to detect the known defect; determining a lowest point cloud density from the plurality of point cloud densities at which the known defect is detectable; and setting an inspection point cloud density for inspection of the feature to the lowest point cloud density.

20 Claims, 5 Drawing Sheets

US 11,169,129 B2

SYSTEM AND METHOD FOR CALIBRATING INSPECTION OF A FEATURE ON A PART

TECHNICAL FIELD

The present disclosure relates generally to inspection of produced or manufactured parts, and more particularly to the calibration of the inspection.

BACKGROUND OF THE ART

There are many reasons which may cause a manufactured part to be out of tolerance. Therefore, inspection of manufactured parts is critical to the manufacturing process. When inspection relies on the skill or experience of an operator, the result of the inspection may vary.

Therefore, improvements are needed.

SUMMARY

In accordance with a broad aspect, there is provided a method for calibrating inspection of a feature on a part. The method comprises acquiring, at a plurality of point cloud densities, measurement data from a reference part having a known defect associated with the feature; assessing the measurement data at the plurality of point cloud densities to detect the known defect; determining a lowest point cloud density from the plurality of point cloud densities at which the known defect is detectable; and setting an inspection point cloud density for inspection of the feature to the lowest point cloud density.

In accordance with another broad aspect, there is provided a system for calibrating inspection of a feature on a part. The system comprises a processing unit and a non-transitory computer-readable medium having stored thereon program code. The program code is executable by the processing unit for acquiring, at a plurality of point cloud densities, measurement data from a reference part having a known defect associated with the feature; assessing the measurement data at the plurality of point cloud densities to detect the known defect; determining a lowest point cloud density from the plurality of point cloud densities at which the known defect is detectable; and setting an inspection point cloud density for inspection of the feature to the lowest point cloud density.

Features of the systems, devices, and methods described herein may be used in various combinations, in accordance with the embodiments described herein. More particularly, any of the above features may be used together, in any combination.

BRIEF DESCRIPTION OF THE DRAWINGS

Reference is now made to the accompanying figures in which.

It will be noted that throughout the appended drawings, like features are identified by like reference numerals.

DETAILED DESCRIPTION

There are described herein methods and systems for calibrating inspection of a produced or manufactured part. Calibration refers to setting a standard to be used when inspecting the part. More specifically, a standard is determined for a point cloud density used in acquiring measurement data from the part under inspection.

The part may be produced using a wide variety of techniques, such as but not limited to machining, injection molding, three-dimensional printing, and the like. In some embodiments, the part is a component from a gas turbine engine, such as those used in aircraft. Example gas turbine engines include turboprop engines, turboshaft engines, turbofan engines, and the like. The part may also be used in other industries and/or for other applications.

Figure 1:
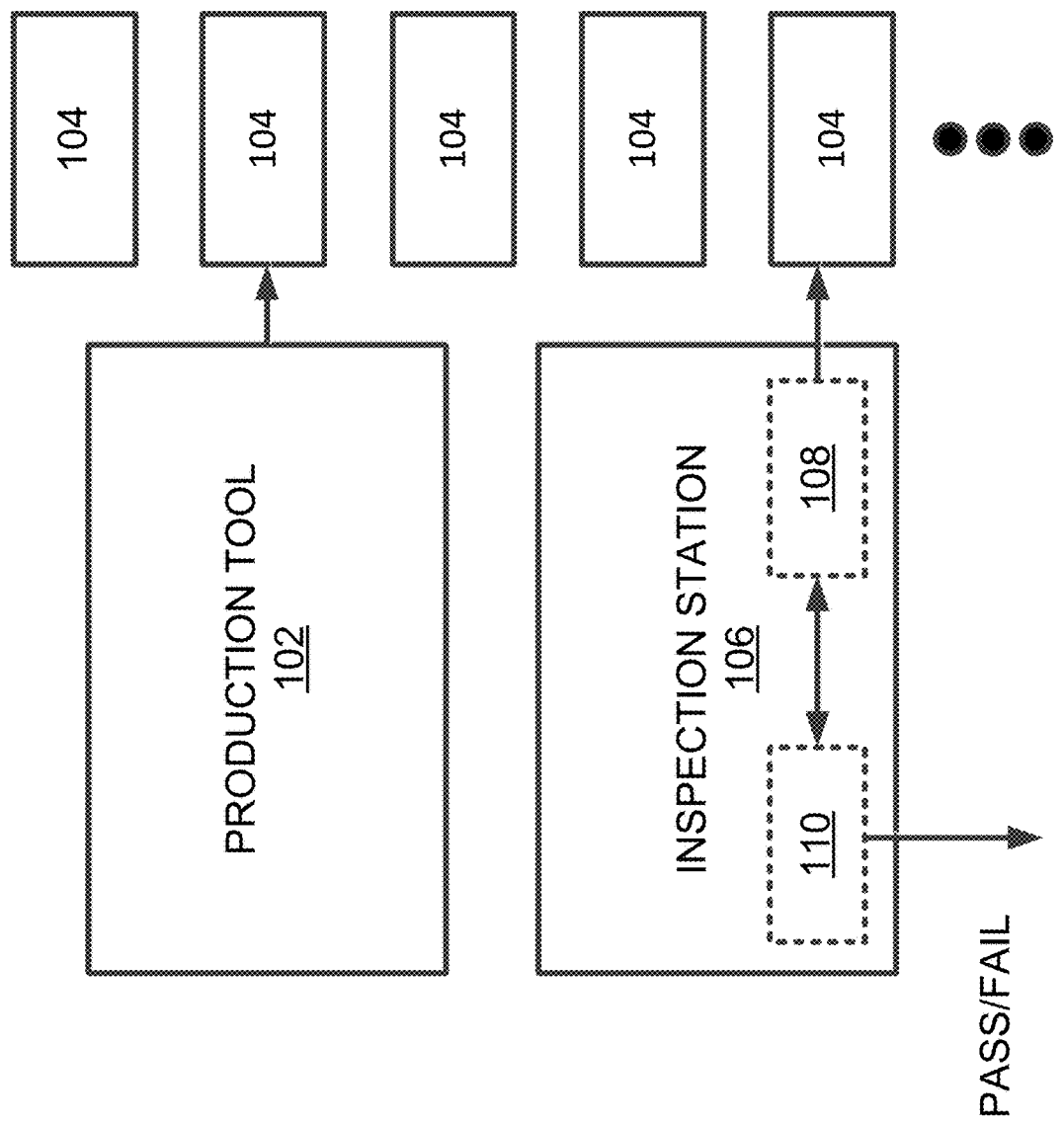
FIG. 1 is a block diagram showing an example production tool and inspection station.

With reference to FIG. 1, there is illustrated an example production tool 102 configured for producing parts 104. Once produced, the parts 104 are provided to an inspection station 106, where inspection is performed. Inspection determines whether the parts 104 as produced are within one or more predetermined tolerance. The parts 104 may be conveyed to the inspection station 106 on a conveyor. The parts 104 may also be carried to the inspection station 106, or transferred thereto using any automated or motorized instrument or equipment.

Once the parts 104 reach the inspection station 106, measurement data is acquired from the parts 104 using one or more data acquisition system 108. Certain types of data acquisition systems 108, such as 3D scanners, sample data points from the surface of the parts. Sets of data points are referred to as point clouds, and point cloud density refers to the number of points per area. A higher point cloud density means a higher resolution and therefore more information regarding the surface sampled. A lower point cloud density means a lower resolution and therefore less information regarding the surface sampled.

A controller 110 receives the measurement data from the data acquisition system 108 and compares the measurement data to reference data defining one or more tolerance for the parts 104. Tolerances may include any manufacturing tolerances, such as but not limited to outside dimensions, thickness, external corner radii, length, straightness, twist, mass, and the like. The reference data may include tolerances for any geometric parameters associated with the parts 104.

Figure 2:
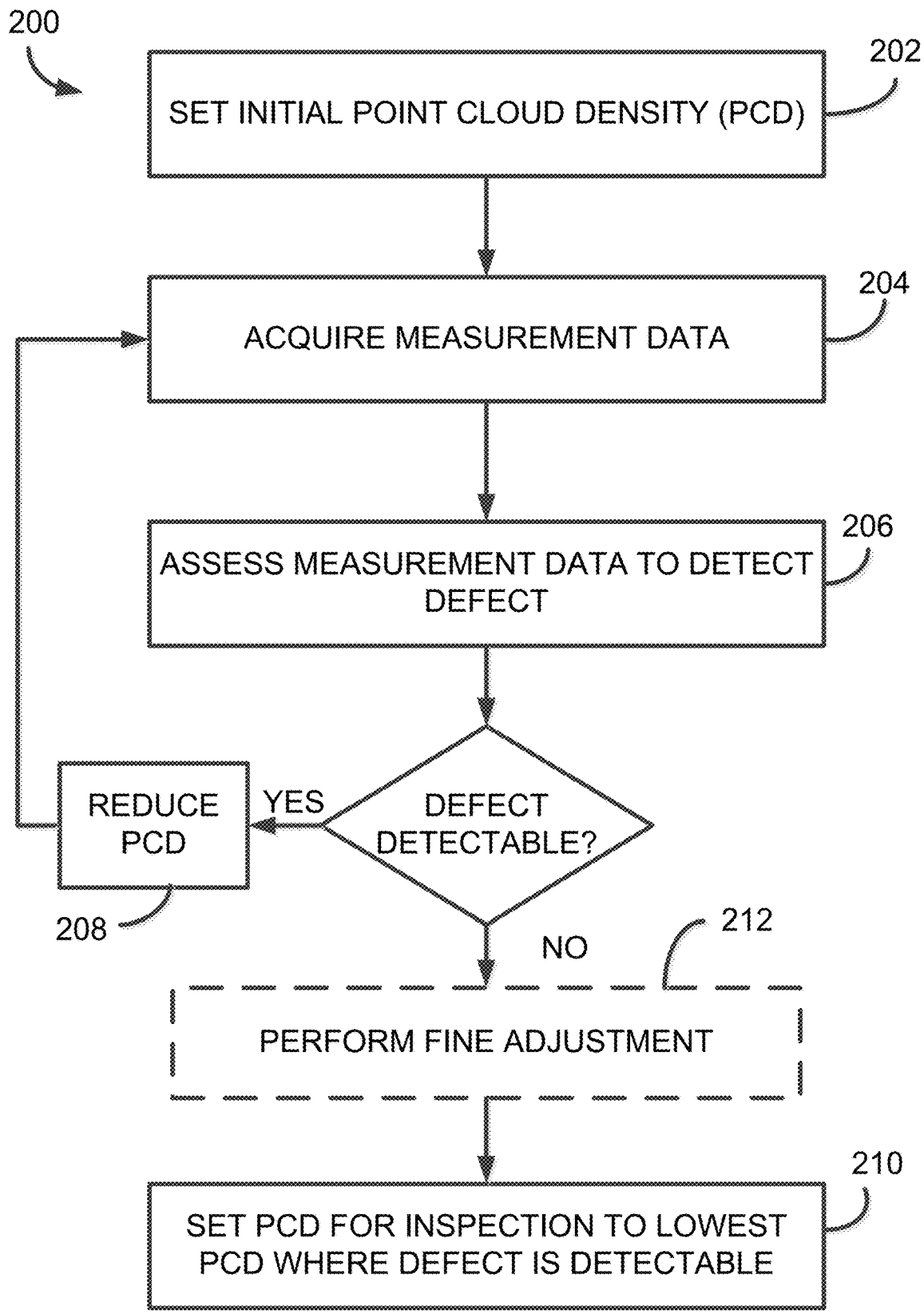
FIG. 2 is a flowchart of an example method for calibrating inspection of a feature of a part.

The controller 110 may be configured to cause the data acquisition system 108 to acquire the measurement data using an optimal point cloud density, also referred to herein as an inspection point cloud density. The optimal point cloud density may be determined using a method for calibrating inspection of a feature on a part. An example embodiment of such a method is illustrated in FIG. 2. The method 200 allows data acquisition, for the purpose of inspection, to be standardized and optimized.

Figure 3B:
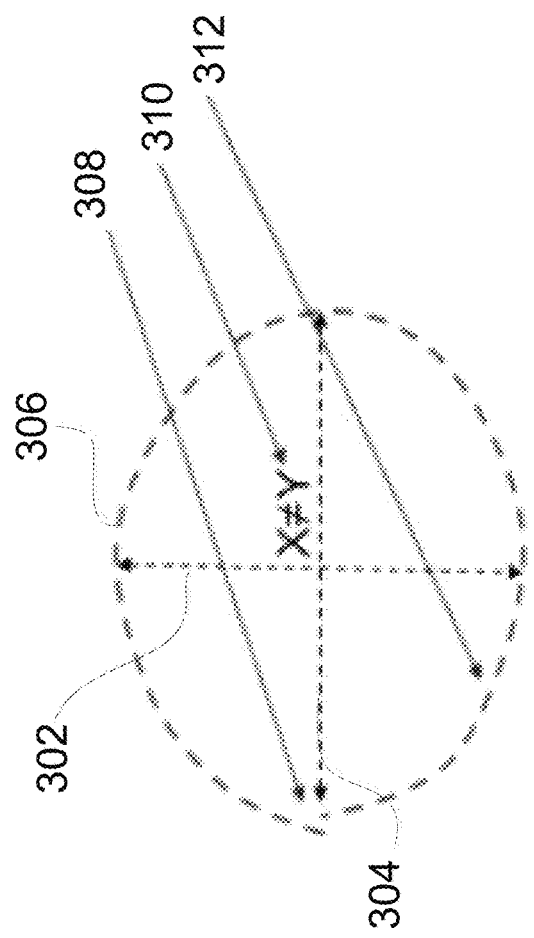
FIGS. 3A-3B are schematic diagrams illustrating a reference part.
Figure 3A:
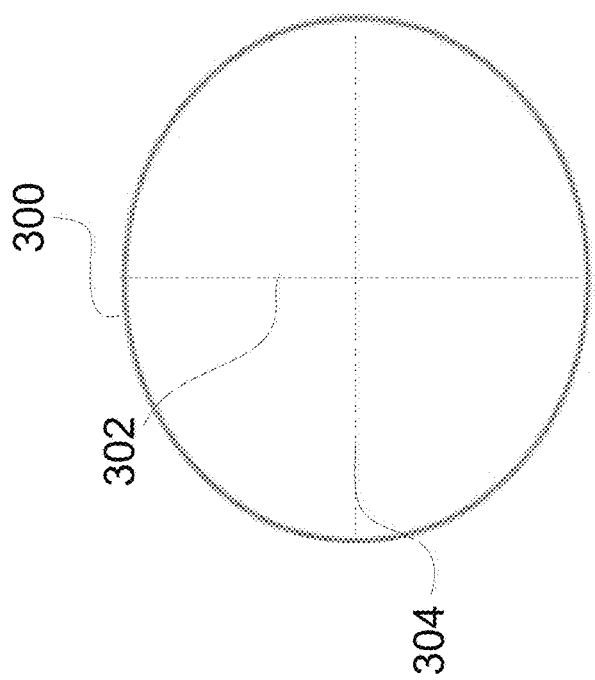

The method 200 is performed on a reference part, which may be virtual or physical. The reference part corresponds to the part 104 to be inspected in accordance with nominal parameters and has one or more known defect associated with one or more feature thereof. An example is shown in FIGS. 3A-3B. FIG. 3A illustrates an example of a feature 300, namely a circular slot, with nominal parameters. The diameter of the slot 300 along the y-axis 302 is equal to the diameter of the slot 300 along the x-axis 304. FIG. 3B shows a reference feature 306, which is the feature 300 with known defects introduced. The shape is deformed such that the diameter along the y-axis 302 does not equal the diameter along the x-axis 304, there are flat regions 312 along the outer perimeter, and there is a mismatch 308 between the top and the bottom hemispheres of the slot. Although three defects are shown in the example of FIG. 3B, more or less than three defects may be introduced to the feature 300 in order to obtain the reference feature 306.

Referring back to FIG. 2, at step 202, a point cloud density (PCD) is set to an initial value. In some embodiments, the initial value is a high value known to result in an oversampling of data. For example, using a resolution of 100% as a baseline, an initial PCD may be set to 95%. Any value that is known to be an oversampling of the data versus what is needed may be used as the initial PCD. A resolution of 100% may be used as the initial PCD. In some embodiments, the initial PCD may vary as a function of the feature. For example, a low complexity feature may have an initial PCD that is much lower than a high complexity feature.

At step 204, measurement data is acquired from the reference part having the known defect associated with the feature. The measurement data is acquired from the reference part in a manner similar to the acquisition of measurement data from the actual part 104 when the part 104 is undergoing inspection. That is to say, the same data acquisition system 108 may be used to acquire the measurement data from the reference part. If the reference part is virtual, the measurement data may be acquired using a virtual data acquisition system 108, such as through simulation or other forms of modelling. In some embodiments, acquiring the measurement data comprises simulating the measurement data or creating the measurement data virtually. It will thus be understood that the measurement data may be acquired physically or virtually, and that virtually acquired data may be simulated or created using other virtual techniques.

At step 206, the measurement data acquired from the reference part is assessed to detect the known defect. Using the example of FIG. 3B, the measurement data is evaluated to determine if the shape of the slot is within a predefined tolerance, for example for the x-axis and y-axis diameters, for the curvature of the outer surface, etc. When the known defect is detectable, the PCD is reduced at step 208 and the steps of data acquisition 204 and detecting the defect 206 are repeated. Steps 204, 206, 208 may be repeated iteratively until it is determined at step 206 that the known defect can no longer be detected at the current PCD. The method 200 then moves on to step 210, where the PCD for inspection is set to the lowest PCD where the known defect is detectable.

In some embodiments, the PCD is reduced at step 208 by a known and fixed amount, for example 2%, 5%, 10%, or the like, and the same amount is used for each iteration. Alternatively, the amount varies at least once throughout the process. For example, the steps may be fixed to a first amount until a certain precision is reached, and then reduced. In another example, larger steps may initially be used, of fixed or varying size, and gradually reduced to smaller steps as the method 200 approaches the lower PCD for detectable defects. In some embodiments, the method 200 comprises determining a step size for a next iteration, based on the result of the past iteration(s).

In some embodiments, once the PCD has been set to a level where the known defect is no longer detectable, a fine adjustment is performed at step 212. The fine adjustment may mean iteratively increasing and reducing the PCD to find the optimal PCD.

In some embodiments, the initial PCD is randomly set. When the known defect is detectable at the initial PCD, the initial PCD is reduced iteratively until the known defect is not detectable. When the known defect is not detectable at the initial PCD, the initial PCD is increased until the known defect is detectable. A fine adjustment may also be performed when going from a PCD that allows detection to a PCD that no longer allows detection, and vice versa.

Figure 4C:
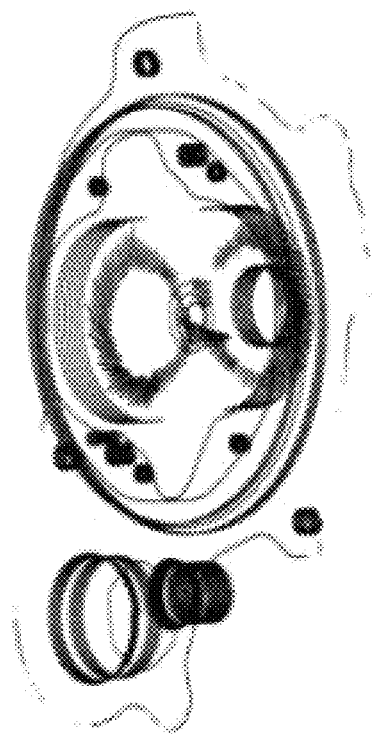
FIGS. 4A-4D are examples of measurement data sets at different point cloud densities.
Figure 4D:
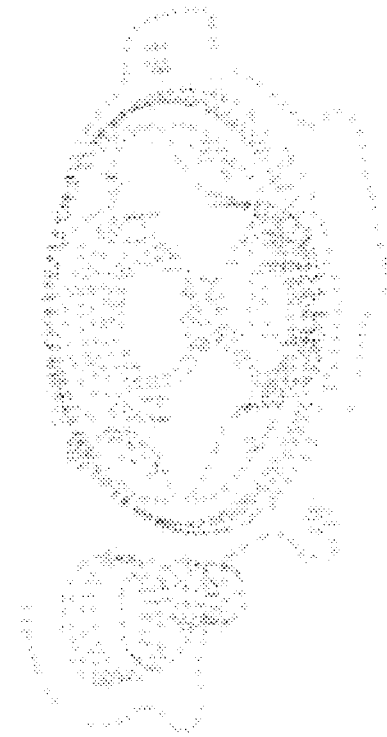
Figure 4A:
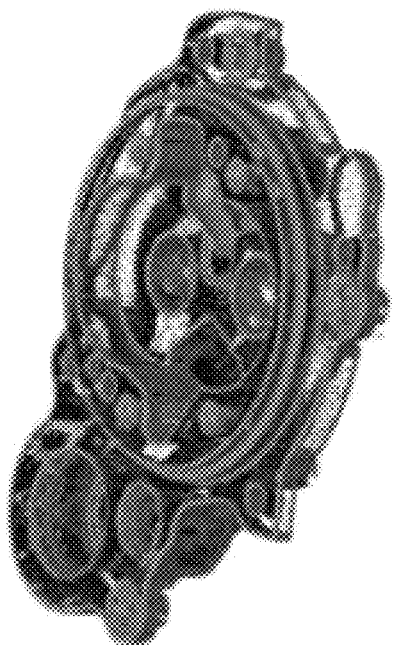
Figure 4B:

With reference to FIGS. 4A-4D, there are illustrated example sets of measurement data at different point cloud densities. FIG. 4A illustrates a highest point cloud density, FIG. 4B is a second highest point cloud density, FIG. 4C is a third highest point cloud density, FIG. 4D is a fourth highest point cloud density.

In some embodiments, additional parameters are considered in setting the PCD for a given feature. For example, the uncertainty of the data acquisition system 108 may be considered, such that for a greater uncertainty, a higher threshold is used to set the PCD. A complexity of a part may also be used to set the threshold for determining the PCD to be used for inspection. Some other parameters that may also be considered are tolerance, feature size, and a nature of the defect.

In some embodiments, a part comprises more than one feature and/or more than one defect. The method 200 may be performed separately for each defect of a feature and the lowest PCD that allows all defects of the feature to be detected is set for use at inspection. The method 200 may also be performed once with all defects of the feature introduced into the reference part. The method 200 may be performed separately for each feature and the lowest PCD that allows all defects of all features to be detected is set for use at inspection. Alternatively, each feature is assigned its own PCD for use at inspection. For example, one surface of a part 104 may be sampled using a first PCD while another surface of the same part 104 may be sampled using a second PCD. Other embodiments may also apply.

Figure 5:
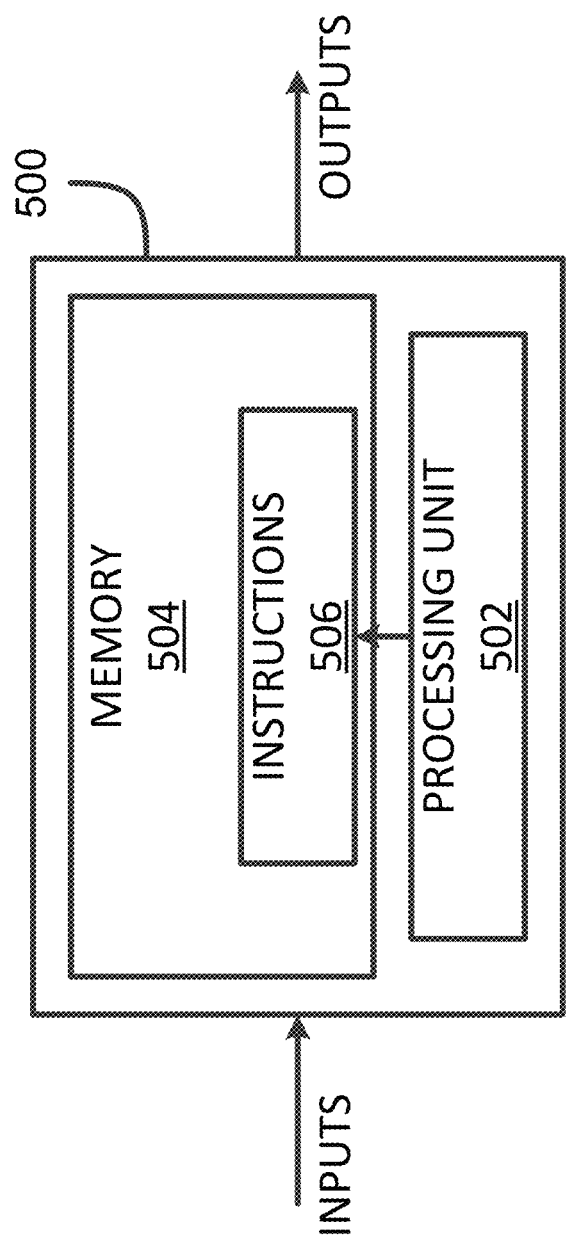
FIG. 5 is a block diagram of an example computing device for performing the method of FIG. 2.

With reference to FIG. 5, an example of a computing device 500 is illustrated. The method 200 may be implemented with one or more of the computing devices 500. The computing device 500 comprises a processing unit 502 and a memory 504 which has stored therein computer-executable instructions 506. The processing unit 502 may comprise any suitable devices configured to implement the method 600 or any variants thereof, such that instructions 506, when executed by the computing device 500 or other programmable apparatus, may cause the functions/acts/steps performed as part of the method 200 to be executed. The processing unit 502 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 502 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 706 executable by processing unit 502.

The methods and systems for calibrating inspection of a feature on a part described herein may be implemented in a high level procedural or object oriented programming or scripting language, or a combination thereof, to communicate with or assist in the operation of a computer system, for example the computing device 500. Alternatively, the methods and systems for calibrating inspection of a feature on a part may be implemented in assembly or machine language. The language may be a compiled or interpreted language. Program code for implementing the methods and systems may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems may also be considered to be implemented by way of a non-transitory computer-readable storage medium having a computer program stored thereon. The computer program may comprise computer-readable instructions which cause a computer, or more specifically the processing unit 502 of the computing device 500, to operate in a specific and predefined manner to perform the functions described herein, for example those described in the method 200.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The embodiments described in this document provide non-limiting examples of possible implementations of the present technology. Upon review of the present disclosure, a person of ordinary skill in the art will recognize that changes may be made to the embodiments described herein without departing from the scope of the present technology. For example, the method may be used within a method for inspecting a part, whereby the inspection point cloud density is determined and then the part is inspected using the inspection point cloud density. In another example, the method may be implemented by the controller 110. Yet further modifications could be implemented by a person of ordinary skill in the art in view of the present disclosure, which modifications would be within the scope of the present technology.

The invention claimed is:

1. A method for calibrating inspection of a feature on a part, the method comprising:
    acquiring, using a data acquisition system, at a plurality of point cloud densities, measurement data from a reference part having a known defect associated with the feature;
    assessing the measurement data at the plurality of point cloud densities to detect the known defect;
    determining a lowest point cloud density from the plurality of point cloud densities at which the known defect is detectable; and
    setting an inspection point cloud density of the data acquisition system for inspection of the feature to the lowest point cloud density.

2. The method of claim 1, wherein acquiring the measurement data at the plurality of point cloud densities comprises setting an initial point cloud density of the data acquisition system and reducing the initial point cloud density iteratively.

3. The method of claim 2, wherein reducing the initial point cloud density iteratively comprises reducing at each iteration by fixed and predetermined amounts.

4. The method of claim 2, wherein reducing the initial point cloud density iteratively comprises reducing until the known defect is not detectable.

5. The method of claim 4, further comprising performing a fine adjustment by increasing and reducing the point cloud density to find the lowest point cloud density.

6. The method of claim 1, wherein acquiring the measurement data at the plurality of point cloud densities comprises acquiring the measurement data from a virtual reference part.

7. The method of claim 1, wherein the method is repeated for additional features of the part, and each feature has an associated inspection point cloud density.

8. The method of claim 1, wherein the method is repeated for additional features of the part, and the lowest point cloud density that can detect all of the additional features is used with the data acquisition system for the inspection of the feature.

9. The method of claim 1, wherein determining the lowest point cloud density comprises using a higher point cloud density when the data acquisition system has a higher uncertainty and a lower point cloud density when the data acquisition system has a lower uncertainty.

10. The method of claim 1, wherein determining the lowest point cloud density comprises using a higher point cloud density when the feature on the part has a higher complexity and a lower point cloud density when the feature on the part has a lower complexity.

11. A system for calibrating inspection of a feature on a part, the system comprising:
    a processing unit; and
    a non-transitory computer-readable medium having stored thereon program code which when executed by the processing unit, configure the processing unit for:
        acquiring, using a data acquisition system, at a plurality of point cloud densities, measurement data from a reference part having a known defect associated with the feature;
        assessing the measurement data at the plurality of point cloud densities to detect the known defect;
        determining a lowest point cloud density from the plurality of point cloud densities at which the known defect is detectable; and
        setting an inspection point cloud density of the data acquisition system for inspection of the feature to the lowest point cloud density.

12. The system of claim 11, wherein acquiring the measurement data at the plurality of point cloud densities comprises setting an initial point cloud density of the data acquisition system and reducing the initial point cloud density iteratively.

13. The system of claim 12, wherein reducing the initial point cloud density iteratively comprises reducing at each iteration by fixed and predetermined amounts.

14. The system of claim 12, wherein reducing the initial point cloud density iteratively comprises reducing until the known defect is not detectable.

15. The system of claim 14, wherein the program code is further executable for performing a fine adjustment by increasing and reducing the point cloud density to find the lowest point cloud density.

16. The system of claim 11, wherein acquiring the measurement data at the plurality of point cloud densities comprises acquiring the measurement data from a virtual reference part.

17. The system of claim 11, wherein the acquiring, assessing, determining, and setting is repeated for additional features of the part, and each feature has an associated inspection point cloud density.

18. The system of claim 11, wherein the acquiring, assessing, and determining is repeated for additional features of the part, and setting the inspection point cloud density comprises selecting the lowest point cloud density that can detect all of the additional features.

19. The system of claim 11, wherein determining the lowest point cloud density comprises using a higher point cloud density when the data acquisition system has a higher uncertainty and a lower point cloud density when the data acquisition system has a lower uncertainty.

20. The system of claim 11, wherein determining the lowest point cloud density comprises using a higher point cloud density when the feature on the part has a higher complexity and a lower point cloud density when the feature on the part has a lower complexity.

* * * * *